US008617372B2

(12) United States Patent
West et al.

(10) Patent No.: US 8,617,372 B2
(45) Date of Patent: Dec. 31, 2013

(54) ARRAY-TYPE $NH_3$ SENSOR

(75) Inventors: David Lawrence West, Oak Ridge, TN (US); Frederick Charles Montgomery, Oak Ridge, TN (US); Timothy R. Armstrong, Clinton, TN (US); Robert J. Warmack, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 50 days.

(21) Appl. No.: 13/046,412

(22) Filed: Mar. 11, 2011

(65) Prior Publication Data
US 2012/0228138 A1 Sep. 13, 2012

(51) Int. Cl.
G01N 27/407 (2006.01)

(52) U.S. Cl.
USPC ........... 204/421; 204/422; 204/423; 204/424; 204/425; 73/23.31; 73/23.32

(58) Field of Classification Search
USPC .................. 204/424–429; 73/23.31–23.32
See application file for complete search history.

(56) References Cited

U.S. PATENT DOCUMENTS

| | | |
|---|---|---|
| 4,005,001 A | 1/1977 | Pebler |
| 4,134,818 A | 1/1979 | Pebler et al. |
| 4,190,499 A | 2/1980 | Pebler |
| 4,229,322 A | 10/1980 | Marchant et al. |
| 5,637,543 A | 6/1997 | Iwaya et al. |
| 5,958,304 A | 9/1999 | Khandkar et al. |
| 2006/0073070 A1* | 4/2006 | Montgomery et al. ........ 422/52 |
| 2007/0012566 A1* | 1/2007 | Nair et al. .................... 204/431 |
| 2007/0289870 A1* | 12/2007 | Nair et al. .................... 204/424 |
| 2010/0077833 A1* | 4/2010 | Wang et al. ................. 73/23.31 |
| 2010/0122916 A1 | 5/2010 | Nair et al. |

FOREIGN PATENT DOCUMENTS

WO WO 2006/036838 A2 4/2006

OTHER PUBLICATIONS

E.P. Murray, R. F. Novak, D. J. Kubinski, R. E. Soltis, J. H. Visser, L. Y. Woo, L. P. Martin, R. S. Glass, Investigating the Stability and Accuracy of the Phase Response for NOx Sensing 5% Mg-Modified LaCrO3 Electrodes, 2007, UCRL-CONF-232164.*
Keith J. Albert et al., *Cross-Reactive Chemical Sensor Arrays*, Jun. 24, 2000, American Chemical Society, Chem. Rev. 2000, 100, pp. 2595-2626.
J. E. Anderson et al., *Steady State Characteristics of Oxygen Concentration Cell Sensors Subjected to Nonequilibrium Gas Mixtures*, Feb. 1981, J. Electrochem Soc.: Electrochemical Science and Technology, pp. 294-300.
Claude Delpha et al., *An electronic nose for the discrimination of forane 134a and carbon dioxide in a humidity controlled atmosphere*, Elsevier Science B.V., Sensors and Actuators B 78 (2001), pp. 49-56.

(Continued)

*Primary Examiner* — Bach Dinh
(74) *Attorney, Agent, or Firm* — Brinks, Hofer, Gilson & Lione

(57) ABSTRACT

An array-type sensor that senses $NH_3$ includes non-Nernstian sensing elements constructed from metal and/or metal-oxide electrodes on an $O_2$ ion conducting substrate. In one example sensor, one electrode may be made of platinum, another electrode may be made of manganese (III) oxide ($Mn_2O_3$), and another electrode may be made of tungsten trioxide ($WO_3$). Some sensing elements may further include an electrode made of $La_{0.6}Sr_{0.4}Co_{0.2}Fe_{0.8}O_3$ and another electrode made of $LaCr_{0.95}Mg_{0.05}O_3$.

22 Claims, 7 Drawing Sheets

(56) References Cited

OTHER PUBLICATIONS

Wolfgang Göpel et al., *Trends in the development of solid state amperometric and potentiometric high temperature sensors*, 2000, Elsevier Science B.V., Solid State Ionics 136-137 (2000) pp. 519-531.

Alan R. Hopkins et al., *Detection and Classification Characteristics of Arrays of Carbon Black/Organic Polymer Composite Chemiresistive Vapor Detectors for the Nerve Agent Simulants dimethylmethylphosphonate and Diisopropylmethylphosponate*, Analytical Chemistry, vol. 73, No. 5, Mar. 1, 2001, pp. 884-892.

Geyu Lu et al., *High-temperature hydrogen sensor based on stabilized zirconia and a metal oxide electrode*, Elsevier Science S.A., Sensors and Actuators B 35-36 (1996), pp. 130-135.

G. Lu et al., *Stabilized zirconia-based sensors using $WO_3$ electrode for detection of NO or $NO_2$*, Elsevier Science S.A. Sensors and Actuators B 65 (2000), pp. 125-127.

Brent T. Marquis et al., *A semiconducting metal oxide sensor array for the detection of $NO_x$ and $NH_3$*, Elsevier Science B.V., Sensors and Actuators B 77 (2001), pp. 100-110.

Jerome F. McAleer et al., *Tin Dioxide Gas Sensors*, J. Chem. Soc., Faraday Trans. 1, 1989 85(4), pp. 783-799.

Norio Miura et al., *Sensing characteristics and mechanism of hydrogen sulfide sensor using stabilized zirconia and oxide sensing electrode*, Elsevier Science S.A., Sensors and Actuators B 34 (1996) pp. 367-372.

Norio Miura et al., *Stabilized zirconia-based sensor using oxide electrode for detection of NOhd x in high-temperature combustion-exhausts*, Elsevier Science B.V., Solid State Ionics 86-88 (1996) pp. 1069-1073.

Norio Miura et al., *Highly selective CO sensor using stabilized zirconia and a couple of oxide electrodes*, Elsevier Science S.A., Sensors and Actuators B 47 (1998) pp. 84-91.

Norio Miura et al., *Mixed-potential-type propylene sensor based on stabilized zirconia and oxide electrode*, Elsevier Science S.A., Electrochemistry Communications 2 (2000), pp. 77-80.

David L. West et al., *"NO-selective" $NO_x$ sensing elements for combustion exhausts*, Elsevier B.V., Sensors and Actuators B 111-112 (2005) pp. 84-90.

Noboru Yamazoe et al., *Environmental gas sensing*, Elsevier Science S.A., Sensors and Actuators B, 20 (1994) pp. 95-102.

Jiun-Chan Yang et al., *High temperature amperometric total $NO_x$ sensors with platinum-loaded zeolite Y electrodes*, Elsevier B.V., Sensors and Actuators B 123 (2007) pp. 929-936.

Björn Timmer et al., *Ammonia sensors and their applications—a review*, Elsevier, Sensors and Actuators B 107 (2005) pp. 666-677.

Ralf Moos, *A Brief Overview on Automotive Exhaust Gas Sensors Based on Electroceramics*, Int. J. Appl. Ceram. Technol., 2 [5] 401-413 (2005).

D.L. West et al., *Detection of $SO_2$ at High Temperature with Electrically Biased, Solid-Electrolyte Sensing Elements*, 2008, ECS Transactions, 16 (11) pp. 301-307.

Mark Wendel et al., *Progress in Creating Stabilized Gas Layers in Flowing Liquid Mercury*, 2008, ASME Fluids Engineering Division Summer Conference, Jacksonville, FL, vol. 2, pp. 23-27.

Timothy R. Armstrong et al., *Development of NOx Sensors for Heavy Vehicle Applications*, Nov. 6, 2006, NOx Sensor CRADA Final Report, pp. 1-8.

Timothy R. Armstrong et al., *C. Development of NOx Sensors for Heavy Vehicle Applications*, FY 2005 Progress Report, Heavy Vehicle Propulsion Materials, pp. 25-29.

Timothy Armstrong et al., *Subtask 1.4 NOx & NH3 Sensor Development* (PIC 714, 639, 635), 2005, Distributed Energy Program, Oak Ridge National Laboratory, pp. 1 of 113, 2 of 113, and 7 of 113.

David L. West et al., *A technique for monitoring $SO_2$ in combustion exhausts: Use of a non-Nernstian sensing element in combination with an upstream catalytic filter*, 2009, Sensors and Actuators B 140, pp. 482-489.

\* cited by examiner

US 8,617,372 B2

ARRAY-TYPE NH₃ SENSOR

GOVERNMENT INTEREST

The inventions were made with government support under Prime Contract No. DE-AC05-00OR22725 awarded by the U.S. Department of Energy. The government has certain rights in inventions.

TECHNICAL FIELD

This disclosure relates generally to chemical sensors and more particularly to an array-type sensor for sensing ammonia ($NH_3$).

BACKGROUND

"Array-type" sensors, comprising a plurality of individual sensing elements, each element having limited selectivity for a particular chemical species, can be used in selective detection. For example, array-type sensors made from carbon black/polymer composites elements, each element sensitive to many different volatile organic compounds, may selectively detect nerve agent stimulants. As another example, arrays made from resistive metal oxide sensing elements, each element sensitive to many different hydrocarbons, may selectively detect forane.

Array-type sensors may also be useful in emission control of combustion exhausts by sensing and/or characterizing the chemistry of the combustion exhaust. Combustion exhausts are complex mixtures, containing several reducing and oxidizing species, including CO, $NO_x$, and hydrocarbons ($C_yH_z$) along with varying amounts of $O_2$, $H_2O$, and $CO_2$. While CO and $C_yH_z$ can be readily ameliorated by oxidation, $NO_x$ is more difficult to remove from exhausts, especially in an $O_2$-containing environment. One technique that is used to reduce the amount of $NO_x$ emitted from the exhaust is selective catalytic reduction (SCR), which uses ammonia ($NH_3$) as a reagent. Under appropriate conditions, $NH_3$ reacts with $NO_x$ to produce nitrogen ($N_2$) and water ($H_2O$). However, escape (or "slip") of $NH_3$ from a SCR system may be harmful, so monitoring for $NH_3$ is desirable.

Resistive metal oxide arrays may selectively detect $NH_3$. However, resistive metal oxide sensing elements may be sensitive to varying [$O_2$] and [$H_2O$] because the transduction mechanism in these sensing elements (change in DC electrical resistivity) relies upon changes in the surface concentration of adsorbed species such as $O_2$. Because combustion exhausts often have varying [$O_2$] and [$H_2O$], resistive oxide sensing elements may not be optimal for use with combustion exhausts. Resistive oxide sensing elements may lose their effectiveness above about 500° C.

DETAILED DESCRIPTION

An array-type sensor senses $NH_3$. The sensor array may use non-Nernstian sensing elements constructed from metal and/or metal-oxide electrodes on an $O_2$ ion conducting substrate, such as yttria-stabilized zirconia (YSZ). These non-Nernstian sensing elements, which individually may comprise a pair of electrodes, may produce measurable DC voltages (usually about 10-100 mV) for example, in the presence of small, yet non-equilibrium, amounts (usually about 10-1000 $ppm_V$) of reducing (e.g., CO) and/or oxidizing (e.g., $NO_2$) species. In one embodiment, the sensing elements comprise a plurality of electrodes comprising five materials: platinum (Pt), manganese (III) oxide ($Mn_2O_3$), tungsten trioxide ($WO_3$), $La_{0.6}Sr_{0.4}Co_{0.2}Fe_{0.8}O_3$, and $LaCr_{0.95}Mg_{0.05}O_3$. The array-type sensor in this embodiment operates at temperatures within two temperature ranges. A first temperature range is from approximately 550-degrees Celsius to approximately 650-degrees Celsius. A second temperature range is from approximately 650-degrees Celsius to approximately 750-degrees Celsius. In this example embodiment of the array-type sensor, a first set of electrodes are configured to operate at a temperature in the first temperature range, and a second set of electrodes are configured to operate at a temperature in the second temperature range.

The materials and operating temperatures were determined based on exposing various sensing elements (electrode pairs) to mixtures of gases containing $NH_3$, CO, $C_3H_6$, and $NO_x$ at concentrations between about 10 and 300 $ppm_V$, and $O_2$ at a concentration of 7 vol %, the balance of the mixture being $N_2$. The materials used in the electrode pairs included Pt, $Mn_2O_3$, $WO_3$, $La_{0.6}Sr_{0.4}Co_{0.2}Fe_{0.8}O_3$, $LaCr_{0.95}Mg_{0.05}O_3$, $CoCr_2O_4$, $Co_3O_4$, $Fe_2O_3$, $(Cu(Ba))_2Cr_2O_{5\pm\delta}$, and ZnO. When reducing species (e.g., $NH_3$) or oxidizing species (e.g., $NO_2$) were presented to the electrode pairs (e.g., Pt—$WO_3$), typically a DC voltage that varied as ln([Re or Ox]/[$O_2$]), where Re and Ox stand for reducing (e.g., CO) or oxidizing (e.g., $NO_2$) species respectively, was observed. However, the magnitude of the voltage was different depending on the identity of the materials making up the pair, and the operating temperature. There were also cases where the logarithmic dependence was not observed.

Figure 5:
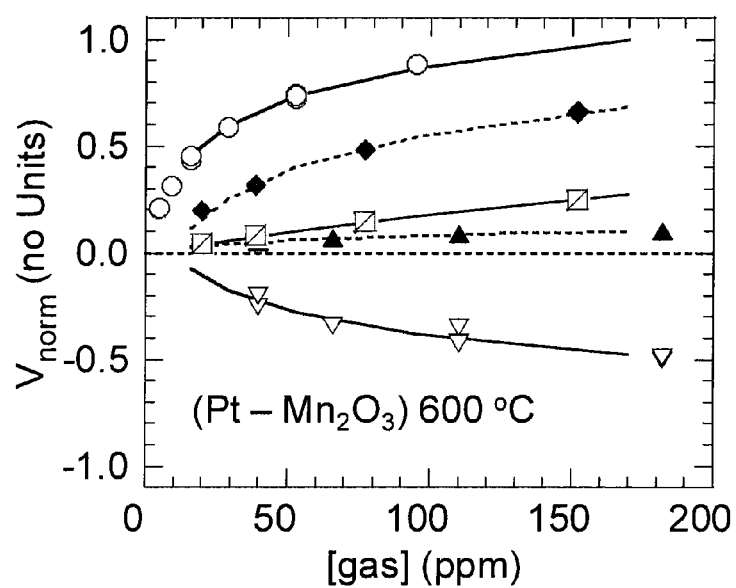
FIG. 5 shows a graph of normalized voltages that were generated between an electrode pair of Pt and $Mn_2O_3$ at 600-degrees Celsius as amounts of $NH_3$, $C_3H_6$, $NO_2$, NO, and CO, were varied.
Figure 6:
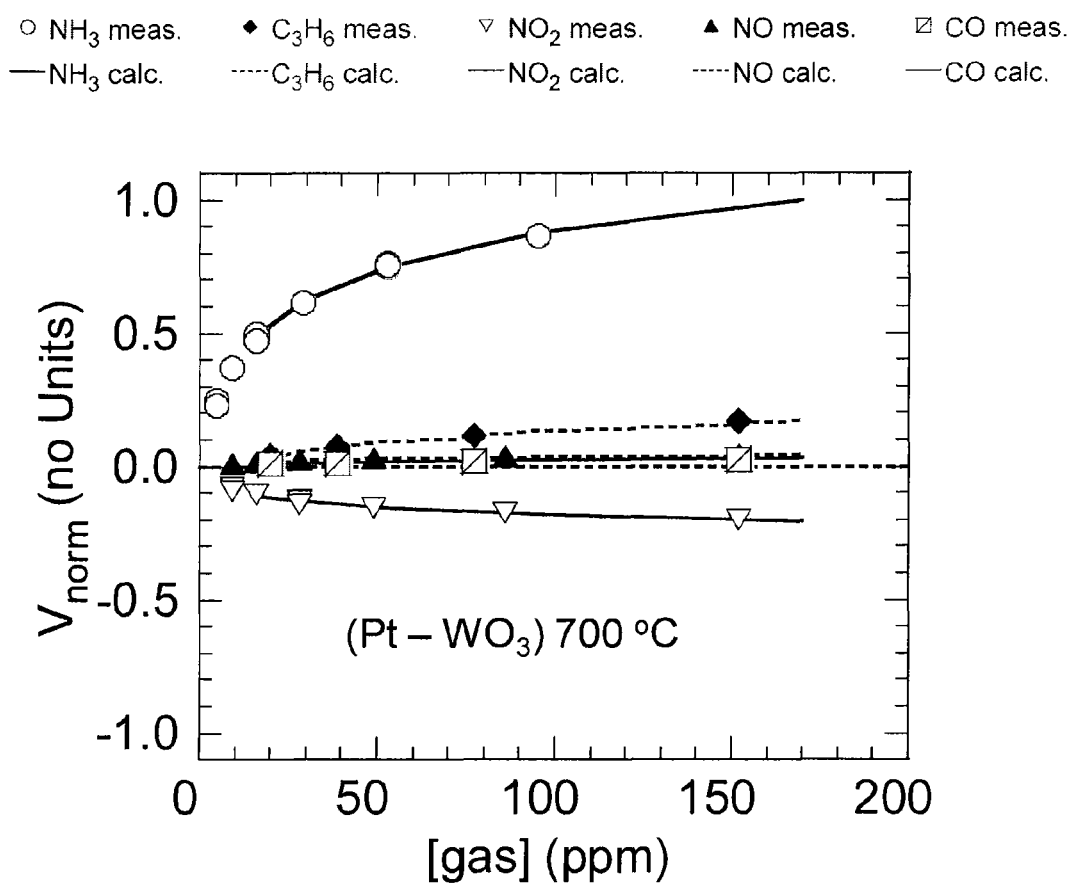
FIG. 6 shows a graph of normalized voltages that were generated between an electrode pair of Pt and $WO_3$ at 700-degrees Celsius as amounts of $NH_3$, $C_3H_6$, $NO_2$, NO, and CO, were varied.
Figure 7:
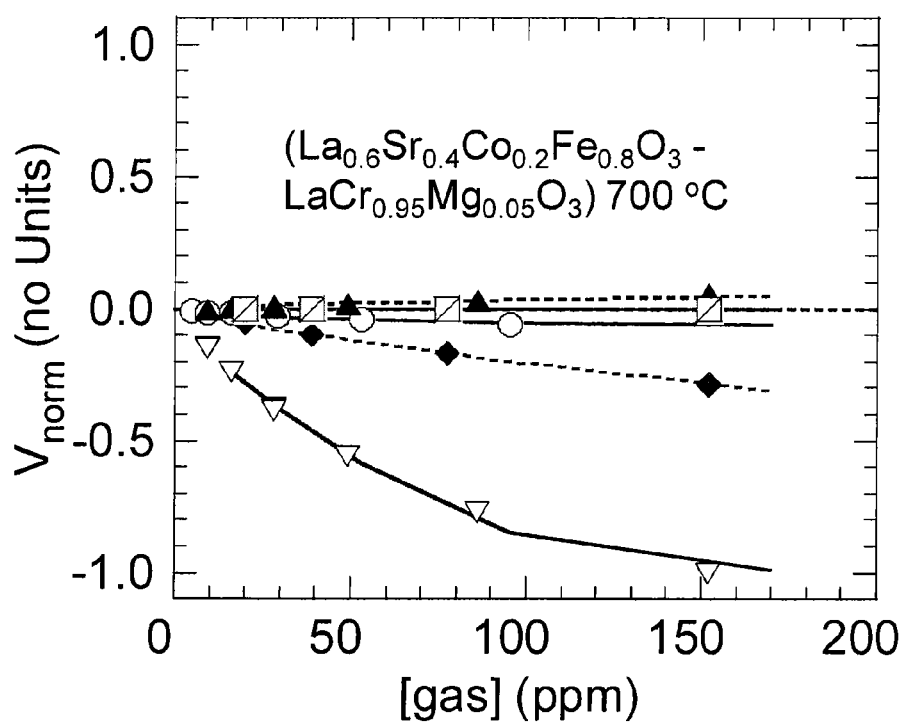
FIG. 7 shows a graph of normalized voltages that were generated between an electrode pair of $La_{0.6}Sr_{0.4}Co_{0.2}Fe_{0.8}O_3$, and $LaCr_{0.95}Mg_{0.05}O_3$ at 700-degrees Celsius as amounts of $NH_3$, $C_3H_6$, $NO_2$, NO, and CO, were varied.

FIGS. 5-7 show graphs of normalized measured voltages that were generated between three of the chosen electrode pairs as amounts of $NH_3$, $C_3H_6$, $NO_2$, NO, and CO, were varied. The three electrode pairs and the temperatures at which they were operated are Pt and $Mn_2O_3$ at 600-degrees Celsius (FIG. 5); Pt and $WO_3$ at 700-degrees Celsius (FIG. 6); and $La_{0.6}Sr_{0.4}Co_{0.2}Fe_{0.8}O_3$, and $LaCr_{0.95}Mg_{0.05}O_3$ at 700-degrees Celsius (FIG. 7). As explained below, these three pairs yielded the most utility for sensing $NH_3$. The graphs shown in FIGS. 5-7 illustrate both logarithmic and non-logarithmic relationships between the amount of gas present and the voltages that were generated between the electrode pairs.

After the voltages were measured for all of the electrode pairs, the measured voltages as a function of the gas concentration were subjected to a kernel or ridge regression analysis, which determined the electrode pairs yielding the most utility for sensing $NH_3$. This procedure identified the most orthogonal electrode pairs, those whose response to $NH_3$ differed the most from the other gases. Three electrode pairs yielded the greatest orthogonality: Pt and $Mn_2O_3$ at approximately 600-degrees Celsius; Pt and $WO_3$ at approximately 700-degrees Celsius; and $La_{0.6}Sr_{0.4}Co_{0.2}Fe_{0.8}O_3$, and $LaCr_{0.95}Mg_{0.05}O_3$ at approximately 700-degrees Celsius. Based on this work, materials and operating temperatures of electrode pairs suitable for incorporation into an array-type sensor for detecting $NH_3$ is determined. The following description describes exemplary, though non-limiting, embodiments of an array-type sensor having a plurality of electrodes that operate at two temperatures, and that comprise Pt, $Mn_2O_3$, $WO_3$, $La_{0.6}Sr_{0.4}Co_{0.2}Fe_{0.8}O_3$, and $LaCr_{0.95}Mg_{0.05}O_3$.

Figure 1:
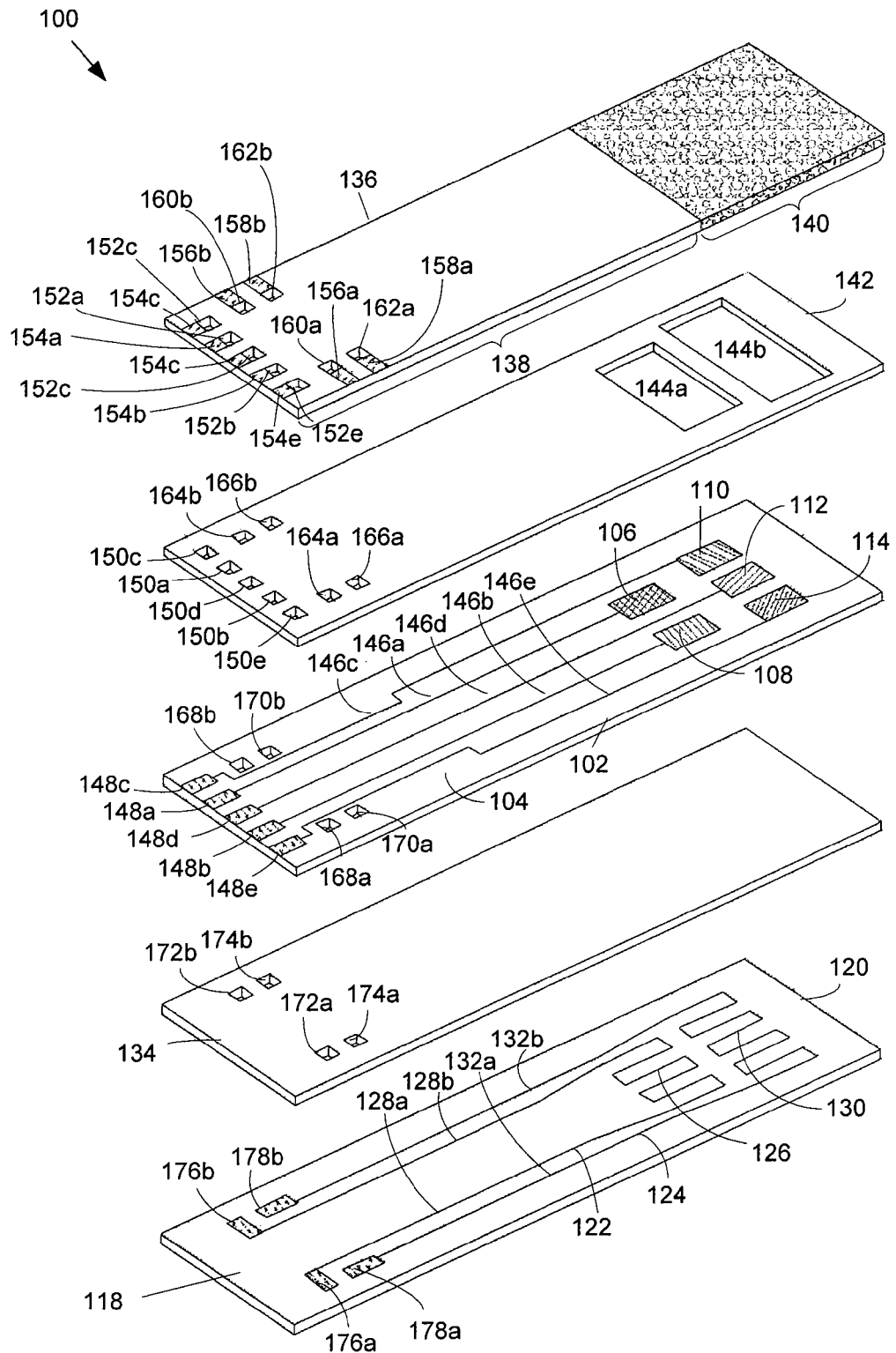
FIG. 1 shows an exploded view of an exemplary array-type sensor for sensing $NH_3$.

FIG. 1 shows an exemplary array-type sensor 100 for sensing $NH_3$. The sensor 100 includes an electrode layer 102 comprising a substrate 104 that comprises an oxygen-ion conducting material, such as $Y_{1-a}Zr_aO_{2-\delta}$, $Sc_{1-a}Zr_aO_{2-\delta}$, $Ca_{1-a}Zr_aO_{2-\delta}$, $Mg_{1-a}Zr_aO_{2-\delta}$, $Gd_{1-b}Ce_bO_{2-\delta}$, $Sm_{1-b}Ce_bO_{2-\delta}$, $La_{1-b}Ce_bO_{2-\delta}$, $Yb_{1-b}Ce_bO_{2-\delta}$, $La_{2-b}Sr_bMo_2O_9$, $La_{2-b}Ba_bMo_2O_9$, $La_{1-b}Sr_bGa_{1-c}Mg_cO_{3-\delta}$, $La_{1-b}Sr_bGa_{1-a-d}Mg_aNi_dO_{3-\delta}$, $La_{1-b}Sr_bGa_{1-a-d}Mg_aCo_dO_{3-\delta}$, $La_{1-b}Sr_bGa_{1-a-d}Mg_aFe_dO_{3-\delta}$, $La_2Mo_{2-e}Nb_eO_9$, $La_2Mo_{2-e}O_9$, or $La_2Mo_{2-e}W_eO_9$ where $0<a<0.2$, $0<b<0.3$, $0<c<0.3$, $a+d<0.3$, and $0<e<1$. In an example embodiment, the substrate 104 has a thickness of one millimeter. However, the thickness of the substrate 104 may vary from about 0.5 millimeters to 1.5 millimeters. The substrate 104 may be produced by tape-casting and sintering. Other methods of production may include, but are not limited to dry pressing, roll compaction, injection molding, etc. followed by appropriate thermal or other treatments to remove processing aids and densify the substrate 104.

The electrode layer 102 further includes an array of electrodes that are disposed on a top planar surface of the substrate 104, including a first electrode 106, a second electrode 108, a third electrode 110, a fourth electrode 112, and a fifth electrode 114. The first electrode 106 comprises platinum (Pt). The second electrode 108 comprises manganese (III) oxide ($Mn_2O_3$). The third electrode 110 comprises tungsten trioxide ($WO_3$). The fourth electrode 112 comprises $La_{0.6}Sr_{0.4}Co_{0.2}Fe_{0.8}O_3$. The fifth electrode 114 comprises $LaCr_{0.95}Mg_{0.05}O_3$.

The array of electrodes 106-114 may be deposited on the substrate 104 by any method. For example, the array of electrodes 106-114 may be deposited onto the substrate 104 using methods of screen-printing a dispersion of electrode material followed by appropriate thermal treatment. Alternate methods of electrode deposition include, but are not limited to sputtering, chemical and physical vapor deposition, spin coating of sol-gel solutions, and pulsed laser deposition. Thickness of the electrodes may be in a range of less than 5 μm to more than 100 μm. The electrode thickness, as well as the microstructure resulting from a particular method of deposition, may be a means of inducing additional orthogonality amongst the sensing elements making up the array.

In the exemplary array-type sensor 100 shown in FIG. 1, the electrodes 106-114 are configured to operate at two temperatures that are within two different temperature ranges. The first electrode 106 and the second electrode 108 are configured to operate at a first temperature that is within a first temperature range. The third electrode 110, the fourth electrode 112, and the fifth electrode 114 are configured to operate at a second temperature that is within a second temperature range. The first temperature range is from approximately 550-degrees Celsius to approximately 650-degrees Celsius.

Preferably, the first temperature in the first temperature range is approximately 600-degrees Celsius. The second temperature range is from approximately 650-degrees Celsius to approximately 750-degrees Celsius. Preferably, the second temperature in the second temperature range is approximately 700-degrees Celsius.

As shown in FIG. 1, the electrodes 106-114 are disposed on the substrate 104 in two rows, with the first electrode 106 and the second electrode 108 being disposed in a first row, and the third electrode 110, the fourth electrode 112, and the fifth electrode 114 being disposed in a second row. The electrodes 106-114 are configured in two rows so that the first electrode 106 and the second electrode 108 can be operated at the first temperature in the first temperature range, and the third electrode 110, the fourth electrode 112, and the fifth electrode 114 can be operated at the second temperature in the second temperature range. However, this disclosure is not limited to the electrodes 106-114 being disposed in two rows, and any configuration of the electrodes 106-114 on the top surface of the substrate 104 may be used. In addition, the present disclosure is not limited to two operating temperatures. For example, the first electrode 106 may operate at a temperature in the first temperature range and the second electrode 108 may operate at a temperature that is also in the first temperature range but that is different than the temperature at which the first electrode 106 is operating. Similarly, the third electrode 110, the fourth electrode 112, and/or the fifth electrode 114 may operate at different temperatures that are all within the second temperature range.

The electrodes 106-114 may operate at the first and second temperatures by applying heat to the electrodes 106-114 using a heating system 118. In the exemplary embodiment shown in FIG. 1, the heating system 118 is configured as a heater layer 120 of the sensor 100. The heater layer 120 is configured to radiate heat so that the first electrode 106 and the second electrode 108 are at the first temperature, and the third electrode 110, the fourth electrode 112, and the fifth electrode 114 are at the second temperature. The heating system 118 includes a first heater 122 and a second heater 124 disposed on the heater layer 120 of the sensor 100. The heater layer 120 may comprise an electrically insulating and refractory material, such as aluminum (III) oxide $Al_2O_3$ (also referred to as alumina). In an example embodiment, the heater layer 120 has a thickness of one millimeter. However, the thickness of the heater layer 120 may vary from about 0.5 millimeters to 1.5 millimeters. As shown in FIG. 1, the heater layer 120 is disposed below the electrode layer 102. The first heater 122 and a second heater 124 are disposed on a top planar surface of the heater layer 120. In addition, as shown in FIG. 1, the first heater 122 is positioned on the top planar surface of the heater layer 120 under the first electrode 106 and the second electrode 108 when assembled. Similarly, the second heater 124 is positioned on the top planar surface of the heater layer 120 under the third electrode 110, the fourth electrode 112, and the fifth electrode 114 when assembled.

In the exemplary embodiment shown in FIG. 1, the first heater 122 and the second heater 124 are configured as resistive heaters for example. The resistive heaters 122, 124 comprise traces of electrically resistive material. In one example, the resistive heaters 122, 124 are made of platinum. However, other electrically conductive materials may be used, such as copper, gold, aluminum, or conductive polymer. The first heater 122 includes a resistive heating element 126 in connection with leads 128a, 128b. Power is applied to the leads 128a, 128b, causing current to flow through the resistive heating element 126 and resulting in heat generated by the resistive heating element 126. The heat generated by the resistive heating element 126 is transferred to the first electrode 106 and the second electrode 108 when assembled. The amount of heat that is generated depends on the power applied to the leads 128a, 128b. The amount of power that is applied to the leads 128a, 128b is such that the first electrode 106 and the second electrode 108 are at approximately the first temperature. Similarly, the second heater 124 includes a resistive heating element 130 in connection with leads 132a, 132b. Power is applied to the leads 132a, 132b, causing current to flow through the resistive heating element 130 and resulting in heat generated by the resistive heating element 130. The heat generated by the resistive heating element 130 is transferred to the third electrode 110, the fourth electrode 112, and the fifth electrode 108 when assembled. The amount of heat that is generated depends on the power applied to the leads 132a, 132b. The amount of power that is applied to the leads 132a, 132b is such that the third electrode 110, the fourth electrode 112, and the fifth electrode 114 are approximately at the second temperature. The first heater 122 and the second heater 124 may be disposed on the heating layer 120 by any technique. For example, the first heater 122 and the second heater 124 may be laminated to the heating layer 120, etched into the heating layer 120, or inked using an electrically resistive polymer on the heating layer 120.

The power that is supplied to the first heater 122 and/or the second heater 124 may be supplied from one or more power sources of the system in which the sensor 100 is used. For example, if the sensor 100 is used in an exhaust system of a vehicle to detect $NH_3$ in the exhaust, then the power source may be a system component of the vehicle. As an example, the system component may be an emissions control component of the vehicle.

Although the heating system 118 of the exemplary embodiment shown in FIG. 1 includes two heaters, the first heater 122 and the second heater 124, the heating system 118 is not limited to two heaters. As explained above, the electrodes 106-114 may be disposed on the top planar surface of the substrate 104 in any configuration. Any number of heaters may be used to heat the electrodes 106-114 to the first and second temperatures. One heater may be used to heat one, two, or three electrodes or any combination thereof. In an alternative embodiment, the heating system 118 is a heat source that is external to the sensor 100.

The exemplary embodiment of the sensor 100 shown in FIG. 1 further includes an insulating layer 134. As shown in FIG. 1, the insulating layer is disposed in between the electrode layer 102 and the heater layer 120. The insulating layer 134 prevents the electrode layer 102 from shorting out the heater layer 120. The insulating layer 134 may comprise an electrically insulating and refractory material, such as $Al_2O_3$. Other materials having electrically insulating and refractory properties may be used. Also, the insulating layer 134 may have a thickness of 0.5 millimeters, although other thicknesses may be used.

The exemplary embodiment of the sensor 100 shown in FIG. 1 further includes a cover layer 136 that is disposed above the electrode layer 102. The cover layer 136 includes a porous portion 140. As shown FIG. 1, the porous portion 140 is positioned over the electrodes 106-114. The size and shape of the porous portion 140 is based on the configuration of the electrodes 106-114 on the substrate 104. The porous portion 140 allows for the diffusion of gas, including $NH_3$, from the environment surrounding the sensor 100 to interact with the electrodes 106-114. The porous portion 140 is used to prevent unwanted materials from being deposited on the electrodes 106-114. Unwanted materials may include dirt, soot, particulates or generally any material that could be deposited on the sensor 100 and prevent the sensor 100 from functioning properly. In addition, where the sensor 100 is used in an exhaust system, the porous portion 140 may be used to even out or normalize pressure from the flow of the exhaust that the sensor 100 experiences in order to reduce and/or minimize any variation in the response of the sensor 100 due to the flow of the exhaust. The porous portion 140 may be made of any material that allows for diffusion of the gas in the environment surrounding the sensor, such as a porous, partially sintered layer of magnesium aluminum oxide ($MgAl_2O_4$), a refractory oxide with the spinel structure. In addition, the cover layer 136 further comprises a cover portion 138, which comprises the portion of the cover layer 136 that is not composed of the porous material. The cover portion 138 may comprise an insulating and refractory material such as $Al_2O_3$. Other materials having insulating and/or refractory characteristics may be used.

The exemplary embodiment of the sensor 100 shown in FIG. 1 further includes a spacing layer 142 that is disposed in between the cover layer 136 and the electrode layer 102. The spacing layer 142 may be used to help keep the cover layer 136 and the electrode layer 102 centered when the layers are heated at very high temperatures during manufacture of the sensor 100. The spacing layer 142 comprises an electrically insulating and refractory material, such as $Al_2O_3$. In addition, the spacing layer 142 includes a cutout portion 144. The cutout portion 144 is configured to provide spacing in between the porous portion 140 and the electrodes 106-114. In the exemplary embodiment shown in FIG. 1, the cutout portion 144 includes a first cutout 144a and a second cutout 144b in this example. The first cutout 144a is disposed over the electrodes operating at the first temperature—i.e., the first electrode 106 and the second electrode 108. The second cutout 144b is disposed over the electrodes operating at the second temperature—i.e., the third electrode 110, the fourth electrode 112, and the fifth electrode 114. Although two cutouts, first cutout 144a and second cutout 144b are shown in FIG. 1, the present disclosure is not limited to two cutouts. For example, the cutout portion 144 may comprise a single cutout disposed over all of the electrodes 106-114.

Referring back to the electrode layer 102, the electrode layer 102 further includes wires 146 in communication with the electrodes 106-114. A first wire 146a is in communication with the first electrode 106. A second wire 146b is in communication with the second electrode 108. A third wire 146c is in communication with the third electrode 110. A fourth wire 146d is in communication with the fourth electrode 112. A fifth wire 146e is in communication with the fifth electrode 114. The wires 146 extend from the electrodes 106-114 to pads 148. The first wire 146a is in communication with a first pad 148a. The second wire 146b is in communication with a second pad 148b. The third wire 146c is in communication with a third pad 148c. The fourth wire 146d is in communication with a fourth pad 148d. The fifth wire 146e is in communication with a fifth pad 148e. As shown in FIG. 1, one end of the first wire 146a is electrically connected to the first electrode 106 and the other end of the first wire 146a is electrically connected to the first pad 148a; one end of the second wire 146b is electrically connected to the second electrode 108 and the other end of the second wire 146b is electrically connected to the second pad 148b; one end of the third wire 146c is electrically connected to the third electrode 110 and the other end of the third wire 146c is electrically connected to the third pad 148c; one end of the fourth wire 146d is electrically connected to the fourth electrode 112 and the other end of the fourth wire 146d is electrically connected to the fourth pad 148d; and one end of the fifth wire 146e is electrically connected to the fifth electrode 114 and the other end of the fifth wire 146e is electrically connected to the fifth pad 148e.

Referring back to the spacing layer 142, the spacing layer 142 may further include vias 150. Vias may comprise holes in a layer that are in electrical communication with conductors, such as transmission lines, contacts, or other vias that are disposed on the same or a different layer. Vias may be plated with a conductive material, such as, although not limited to, platinum, copper, gold, silver, or conductive polymer. As shown in FIG. 1, the vias 150 are disposed over the pads 148. The vias 150, being disposed over the pads 148, are in electrical communication with the pads 148 when assembled. A first via 150a is in electrical communication with the first pad 148a. A second via 150b is in electrical communication with the second pad 148b. A third via 150c is in electrical communication with the third pad 148c. A fourth via 150d is in electrical communication with the fourth pad 148d. A fifth via 150e is in electrical communication with the fifth via 148e.

Referring back to the cover layer 136, the cover layer further includes vias 152. The vias 152 are disposed over the vias 150 when assembled. A first via 152a is in electrical communication with the first via 150a. A second via 152b is in electrical communication with the second via 150b. A third via 152c is in electrical communication with the third via 150c. A fourth via 152d is in electrical communication with the fourth via 150d. A fifth via 152e is in electrical communication with the fifth via 150e. The cover layer 136 further includes contacts 154 that are connected to the vias 152. A first contact 154a is in electrical communication with the first via 152a. A second contact 154b is in electrical communication with the second via 152b. A third contact 154c is in electrical communication with the third via 152c. A fourth contact 154d is in electrical communication with the fourth via 152d. A fifth contact 154e is in electrical communication with the fifth via 154e.

As explained power may be supplied to the sensor 100 to deliver current to the heaters 122, 124 and generate and/or radiate heat. In the exemplary embodiment shown in FIG. 1, current is delivered to the first heater 122 by applying power to contacts 156a, 156b. Current is delivered from contacts 156a, 156b, through vias 160a, 160b on the cover layer 136, through vias 164a, 164b on the spacing layer 142, through vias 168a, 168b on the electrode layer 102, through vias 172a, 172b on the insulating layer 134, and to pads 176a, 176b, which are in connection with the leads 128a, 128b of the first heater 122. Similarly, current is delivered to the second heater 124 by applying power to contacts 158a, 158b. Current is delivered from contacts 158a, 158b, through vias 162a, 162b on the cover layer 136, through vias 166a, 166b on the spacing layer 142, through vias 170a, 170b on the electrode layer 102, through vias 174a, 174b on the insulating layer 134, and to pads 178a, 178b, which are in connection with the leads 132a, 132b of the second heater 124. In an alternative embodiment, the pads 178a, 178b are in connection with contacts on a bottom planar surface of the heater layer 120. Power may be applied to the contacts on the bottom surface of the heater layer (not shown), which sends current to the heaters 122, 124.

In operation, a DC voltage is generated between any two of the electrodes 106-114 in the presence of $NH_3$ and other reducing or oxidizing species. The DC signal that is generated between two electrodes is transmitted along the wires 146 and to the pads 148. The DC signal is transmitted up through the vias 150 and the vias 152 and to the contacts 154. Any device that is capable of measuring DC voltage, preferably at time intervals, may be connected to the contacts 154 to measure DC voltage that is generated between any two electrodes, for example 106 and 108, amongst the plurality of electrodes 106-114. The measurement device may also be capable of storing as data the measured voltages and/or transmitting information containing the voltage measurements to a storage device and/or a processing device, such as a computer.

Each pair of electrodes selected from the set 106-114 produces a unique response voltage in the presence of $NH_3$ that is different in polarity and/or magnitude from other response voltages that are generated by other pairs of electrodes. For example, for a given amount of $NH_3$, the voltage generated between the first electrode 106 and the second electrode 108 is different from the voltage generated between the second electrode 108 and the third electrode 110, which is different from voltage generated between the third electrode 110 and the fourth electrode 112, and so on. Based on the different voltage responses between the electrodes, a pattern of response voltages that signals the presence of $NH_3$ may be determined. The pattern of voltage responses may be determined based on the electrodes 106-114 being exposed to $NH_3$ in isolation. In addition or alternatively, the pattern of response voltages may be based on the electrodes 106-114 being exposed to $NH_3$ in combination with other gases, including interferents and/or other gases that may be present in the environment surrounding the sensor, such as $O_2$. For example, in diesel combustion exhaust, interferents CO, $C_3H_6$, and $NO_6$, in addition to oxygen $O_2$, may be present with $NH_3$. The pattern of voltage responses may be determined based on $NH_3$ in combination with $O_2$ and/or one or more of the interferents CO, $C_3H_6$, and $NO_6$. Alternatively or in addition, the pattern may be determined by the electrodes being exposed to one or more of the gases in isolation, and/or varying $O_2$ while holding $NH_3$ and the interferents at constant levels, and/or varying $NH_3$ while holding $O_2$ and the interferents at constant levels. When the sensor 100 is in operation and the electrodes 106-114 are exposed to $NH_3$, voltages generated by the electrodes 106-114 are measured, and the measured voltages are compared with the pattern of voltage responses. Based on the comparison, an amount of $NH_3$ in the environment surrounding the sensor 100 at a given time, and/or a rate of change in the amount of $NH_3$ in the environment over a period of time may be determined.

The length of the sensor 100 may be between approximately three centimeters and six centimeters. The width of the sensor 100 may be between approximately 0.5 centimeters and 2.5 centimeters. However, the length and width of the sensor 100 may be of any dimensions suitable to accommodate the array of electrodes 106-114. The layers of the sensor may be combined using any known manufacturing method, such as by heating the layers at high temperatures.

Figure 2:
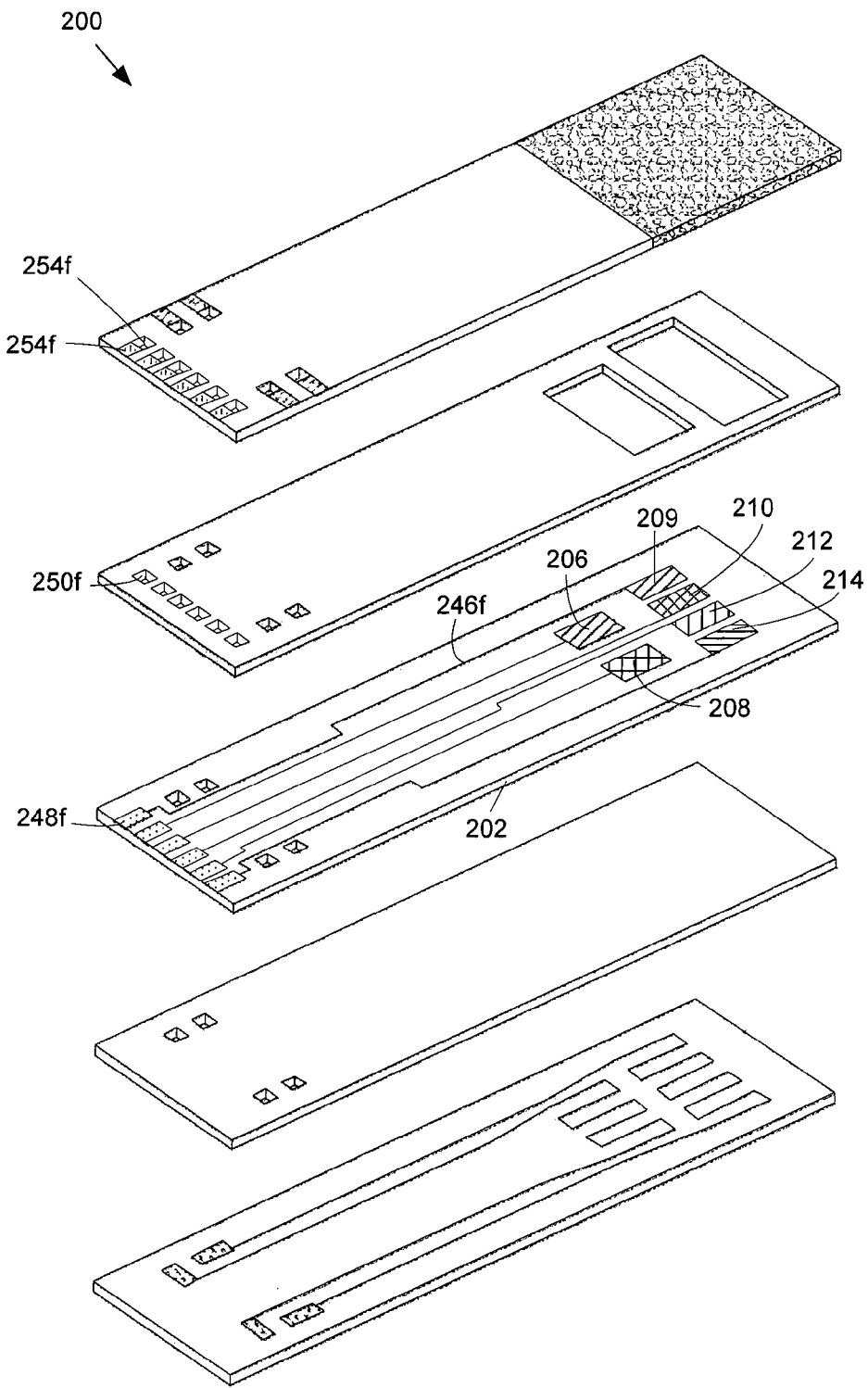
FIG. 2 shows an exploded view of an alternative exemplary embodiment of the array-type $NH_3$ sensor.

FIG. 2 illustrates an alternative embodiment of an array-type sensor 200 for sensing $NH_3$. The sensor 200 is similar to the sensor 100 illustrated in FIG. 1 except that the sensor 200 includes an additional electrode disposed on an electrode layer 202 that is configured to operate at the second temperature. The electrode layer 202 includes six electrodes disposed on a top planar surface of the electrode layer 202. A first electrode 206 comprises platinum (Pt). A second electrode 208 comprises manganese (III) oxide ($Mn_2O_3$). A third electrode 209 comprises platinum (Pt). A fourth electrode 210 comprises tungsten trioxide ($WO_3$). A fifth electrode 212 comprises $La_{0.6}Sr_{0.4}Co_{0.2}Fe_{0.8}O_3$. A sixth electrode 214 comprises $LaCr_{0.95}Mg_{0.05}O_3$. The sensor 200 further includes an additional wire 246f, a pad 248f, vias 250f, 252f, and a contact 254f that are in electrical communication with each other and with the additional platinum electrode 209 to measure DC voltage generated between the additional platinum electrode 209 and any of the other electrodes 206, 208, 210, 212, 214.

Figure 3:
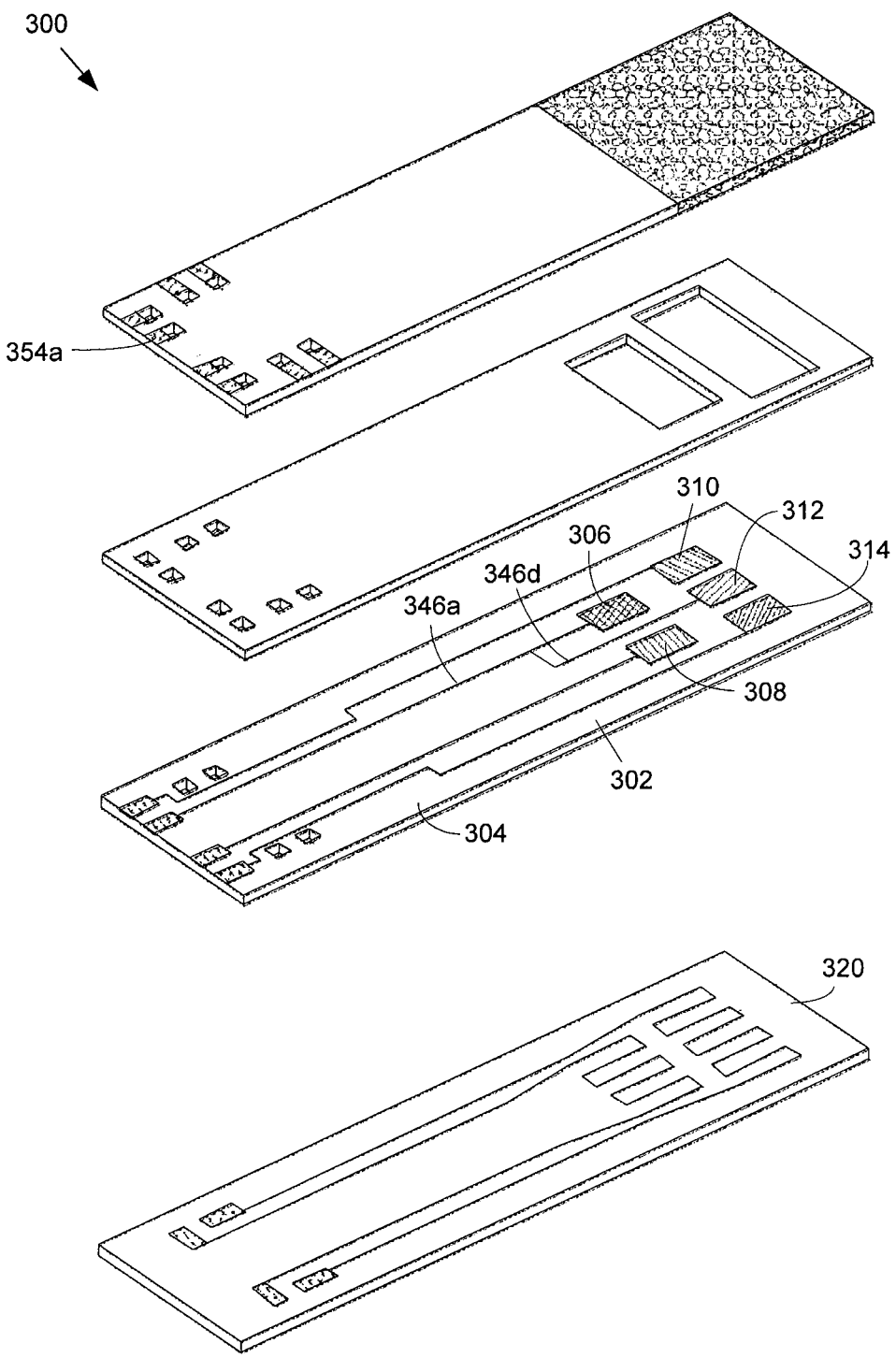
FIG. 3 shows an exploded view of a second alternative exemplary embodiment of the array-type $NH_3$ sensor.

FIG. 3 illustrates another alternative embodiment of an array type sensor 300 for sensing NH$_3$. The sensor 300 is similar to the sensor 100 illustrated in FIG. 1 except that two electrodes are electrically connected together by connecting the wires that are connected to the electrodes. In one example, an electrode configured to operate at a temperature in the first range is connected to an electrode configured to operate at a temperature in the second range. By connecting two electrodes together, only three different voltages from five different electrodes may be measured. Connecting two electrodes together eliminates a wire and pad on the electrode layer, a via on the spacing layer, and a via and a contact on the cover layer, which may simplify a connection from the sensor 300 to a measurement device that is used to measure the DC voltages. In the exemplary embodiment of the sensor 300 shown in FIG. 3, an electrode 306 is connected to another electrode 312 by connecting wire 346a with wire 346d. Contact 354a may be used to measure generated voltage between electrode 306 or electrode 312 and any of the other electrodes 308, 310, 314. In addition, as shown in FIG. 3, depending on the oxygen-ion conducting material of the substrate 304, an insulating layer may not be disposed in between the electrode layer 302 and the heater layer 320. Depending on the oxygen-ion conducting material, the substrate 304 may provide enough insulation in between the electrode layer 302 and the heater layer 320 such that the electrode layer 302 may be disposed directly over the heater layer 320 and an insulating layer is not needed to prevent the heaters from shorting.

Although the sensors 100, 200, 300 illustrated in FIGS. 1, 2, and 3 show five or six electrodes, the array-type sensor of the present disclosure is not limited to five or six electrodes. More than six electrodes may be used, and in general, the array-type sensor may include five or more electrodes, where at least one electrode comprises platinum and is configured to operate in the first temperature range, at least one electrode comprises manganese (III) oxide (Mn$_2$O$_3$) and is configured to operate in the first temperature range, at least one electrode comprises tungsten trioxide (WO$_3$) and is configured to operate in the second temperature range, at least one electrode comprises La$_{0.6}$Sr$_{0.4}$Co$_{0.2}$Fe$_{0.8}$O$_3$ and is configured to operate in the second temperature range, and at least one electrode comprises LaCr$_{0.95}$Mg$_{0.05}$O$_3$ and is configured to operate in the second temperature range.

Figure 4:
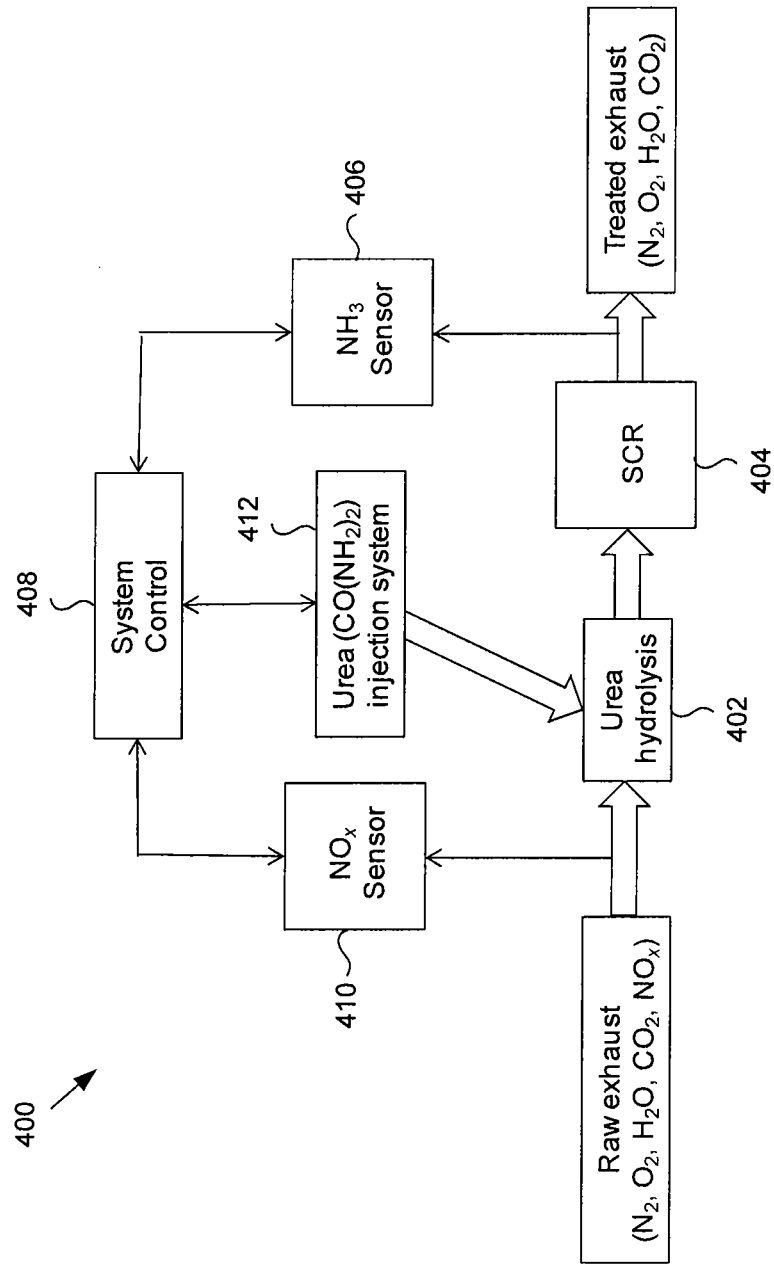
FIG. 4 shows an exemplary exhaust system schematic in which the array-type $NH_3$ sensor may be implemented.

FIG. 4 illustrates a schematic representation of an example exhaust system 400 in which at least one of the array-type sensors as described above may be used. The exhaust system 400 may be stationary, such as an exhaust system of a power plant. Alternatively, the exhaust system 400 may be mobile, such as an exhaust system of a vehicle. As shown in FIG. 4, the exhaust system 400 includes an urea (CO(NH$_2$)$_2$) hydrolysis subsystem 402, which is intended to decompose CO(NH$_2$)$_2$ into NH$_3$ and CO$_2$. The NH$_3$ that is produced reacts with the raw exhaust, containing NO$_x$ in a selective catalytic reduction (SCR) subsystem 404 to convert the NO$_x$ in the raw exhaust to H$_2$O and N$_2$. Treated exhaust, including N$_2$, O$_2$, H$_2$O, and CO$_2$, resulting from the urea hydrolysis and SCR processes, is output from the SCR subsystem 404. In actual exhaust systems, NH$_3$ may escape from the SCR process (referred to as ammonia slip). To sense the NH$_3$ that has escaped, an array-type NH$_3$ sensor 406 as described above is configured in the exhaust system 400 to be at or near an output of the SCR subsystem 404. A system control 408 is connected to the sensor 406 to measure voltage that was generated from the sensor 406 due to the detected NH$_3$. The control system 408 may also measure voltage generated from a NO sensor 410 used to sense NO$_x$ from the raw exhaust, and/or control an urea injection system 412 that injects urea into the urea hydrolysis subsystem 402. In addition, the control system 408 may generate, store and/or process data associated with the measured voltages from the array-type NH$_3$ sensor 406. Using the voltage data, the system control 408 may characterize the chemistry of the treated exhaust and determine the amount and/or change in the amount of NH$_3$ that is in the treated exhaust.

Various embodiments described herein can be used alone or in combination with one another. The foregoing detailed description has described only a few of the many possible implementations of the present invention. For this reason, this detailed description is intended by way of illustration, and not by way of limitation.

What is claimed is:

1. A method of sensing ammonia (NH$_3$) with an array-type sensor, the array-type sensor comprising a substrate that comprises an oxygen-ion conducting material, and an array of electrodes disposed on the substrate, the method comprising:
    operating a first electrode of the array of electrodes at a first temperature that is in a first temperature range, the first temperature range being from approximately 550-degrees Celsius to approximately 650-degrees Celsius, the first electrode comprising platinum (Pt);
    operating a second electrode of the array of electrodes at a second temperature that is in the first temperature range, the second electrode comprising manganese (III) oxide (Mn$_2$O$_3$);
    operating a third electrode of the array of electrodes at a third temperature that is in a second temperature range, the second temperature range being from approximately 650-degrees Celsius to approximately 750-degrees Celsius, the third electrode comprising tungsten trioxide (WO$_3$);
    operating a fourth electrode of the array of electrodes at a fourth temperature that is in the second temperature range, the fourth electrode comprising La$_{0.6}$Sr$_{0.4}$Co$_{0.2}$Fe$_{0.8}$O$_3$;
    operating a fifth electrode of the array of electrodes at a fifth temperature that is in the second temperature range, the fifth electrode comprising LaCr$_{0.95}$Mg$_{0.05}$O$_3$; and
    sensing, with the array-type sensor, ammonia (NH$_3$) in response to the first electrode operating at the first temperature, the second electrode operating at the second temperature, the third electrode operating at the third temperature, the fourth electrode operating at the fourth temperature, and the fifth electrode operating at the fifth temperature.

2. The method of claim 1, wherein the oxygen-ion conducting material comprises yttria-stabilized zirconia (YSZ).

3. The method of claim 1, wherein the first temperature and the second temperature are substantially the same, and wherein the third temperature, the fourth temperature, and the fifth temperature are substantially the same.

4. The method of claim 3, wherein the first temperature and second temperature are both approximately 600-degrees Celsius, and wherein the third temperature, the fourth temperature, and the fifth temperature are each approximately 700-degrees Celsius.

5. The method of claim 1, further comprising:
    heating, with a heater layer of the array-type sensor, the first electrode to the first temperature, the second electrode to the second temperature, the third electrode to the third temperature, the fourth electrode to the fourth temperature, and the fifth electrode to the fifth temperature.

6. The method of claim 5, wherein the heater layer comprises a first heater and a second heater, and wherein heating comprises:
   heating, with the first heater, the first electrode to the first temperature and the second electrode to the second temperature, wherein the first temperature and the second temperature are substantially the same; and
   heating, with the second heater, the third electrode to the third temperature, the fourth temperature to the fourth temperature, and the fifth electrode to the fifth temperature, wherein the third temperature, the fourth temperature, and the fifth temperature are substantially the same.

7. The method of claim 6, wherein the first heater is disposed under the first electrode and the second electrode, and wherein the second heater is disposed under the third electrode, the fourth electrode, and the fifth electrode.

8. The method of claim 1, wherein the array-type sensor further comprises a cover layer having a porous portion disposed above the array of electrodes, the method further comprising:
   diffusing, through the porous portion of the cover layer, the ammonia ($NH_3$).

9. The method of claim 8, wherein the cover layer further comprises a plurality of contacts in electrical communication with the array of electrodes, the method further comprising:
   generating, between two contacts of the plurality of contacts, a direct current (DC) voltage when the array of electrodes is exposed to the ammonia ($NH_3$),
   wherein sensing the ammonia ($NH_3$) comprises sensing, with the array-type sensor, the ammonia ($NH_3$) in response to generating the DC voltage.

10. The method of claim 1, wherein the array of electrodes further comprises a sixth electrode comprising platinum (Pt), the method further comprising:
   operating the sixth electrode at a sixth temperature that is in the second temperature range.

11. The method of claim 1, wherein one of the first electrode and the second electrode is electrically connected to one of the third electrode, the fourth electrode, and the fifth electrode.

12. A method of sensing ammonia ($NH_3$) in a selective catalytic reduction (SCR) subsystem of an exhaust system, the method comprising:
   positioning an array-type sensor at an output of the SCR subsystem, wherein the array-type sensor comprises a substrate that comprises an oxygen-ion conducting material, and an array of electrodes disposed on the substrate;
   operating a first set of electrodes of the array of electrodes at a first temperature that is in a first temperature range, the first temperature range being from approximately 550-degrees Celsius to approximately 650-degrees Celsius, wherein the first set of electrodes comprises a first electrode comprising platinum (Pt) and a second electrode comprising manganese (III) oxide ($Mn_2O_3$);
   operating a second set of electrodes of the array of electrodes at a second temperature that is in a second temperature range, the second temperature range being from approximately 650-degrees Celsius to approximately 750-degrees Celsius, the second set of electrodes comprising a third electrode comprising tungsten trioxide ($WO_3$); a fourth electrode comprising $La_{0.6}Sr_{0.4}Co_{0.2}Fe_{0.8}O_3$; and a fifth electrode comprising $LaCr_{0.95}Mg_{0.05}O_3$; and
   sensing, with the array-type sensor positioned at the output of the SCR subsystem, ammonia ($NH_3$) in response to the first set of electrodes operating at the first temperature and the second set of electrodes operating at the second temperature.

13. The method of claim 12, wherein the oxygen-ion conducting material is yttria-stabilized zirconia (YSZ).

14. The method of claim 12, wherein operating the first set of electrodes at the first temperature comprises operating the first electrode and the second electrode at the same temperature, and wherein operating the second set of electrodes at the second temperature comprises operating the third electrode, the fourth electrode, and the fifth electrode at the same temperature.

15. The method of claim 12, wherein the first temperature is approximately 600-degrees Celsius and the second temperature is approximately 700-degrees Celsius.

16. The method of claim 12, further comprising:
   heating, with a heater layer of the array-type sensor, the first set of electrodes to the first temperature and the second set of electrodes to the second temperature.

17. The method of claim 16, wherein the heater layer comprises a first heater and a second heater, and wherein heating comprises:
   heating, with the first heater, the first set of electrodes to the first temperature; and
   heating, with the second heater, the second set of electrodes to the second temperature.

18. The method of claim 17, wherein the first heater is disposed under the first set of electrodes, and wherein the second heater is disposed under the second set of electrodes.

19. The method of claim 12, wherein the array-type sensor further comprises a cover layer having a porous portion disposed above the array of electrodes, the method further comprising:
   diffusing, through the porous portion of the cover layer, the ammonia ($NH_3$).

20. The method of claim 19, wherein the cover layer further comprises a plurality of contacts in electrical communication with the array of electrodes, the method further comprising:
   generating, between two contacts of the plurality of contacts, a direct current (DC) voltage when the array of electrodes is exposed to the ammonia ($NH_3$),
   wherein sensing the ammonia ($NH_3$) comprises sensing, with the array-type sensor positioned at the output of the SCR subsystem, the ammonia ($NH_3$) in response to generating the DC voltage.

21. The method of claim 12, wherein the plurality of electrodes further comprises at least one sixth electrode comprising platinum (Pt), the method further comprising:
   operating the at least one sixth electrode at the second temperature.

22. The method of claim 12, wherein one of the electrodes in the first set of electrodes is electrically connected to one of the electrodes in the second set of electrodes.

* * * * *